United States Patent [19]

Mandler et al.

[11] Patent Number: 5,385,708
[45] Date of Patent: Jan. 31, 1995

[54] DETERMINATION OF ULTRA LOW LEVELS OF MERCURY

[75] Inventors: Daniel Mandler; Iva Turyan, both of Jerusalem, Israel

[73] Assignee: Yissum Research Development Company of the Hebrew University of Jerusalem, Jerusalem, Israel

[21] Appl. No.: 86,160

[22] Filed: Jul. 2, 1993

[51] Int. Cl.$^6$ .................... G01N 27/26; G01N 33/20
[52] U.S. Cl. .................... 422/82.03; 436/81; 204/418
[58] Field of Search ........... 436/81; 422/82.03, 82.01; 204/412, 403, 418

[56] References Cited

U.S. PATENT DOCUMENTS

| | | | |
|---|---|---|---|
| 4,795,543 | 1/1989 | Stetter et al. | 204/412 |
| 4,797,181 | 1/1989 | Durfor et al. | 204/1 T |
| 5,031,449 | 7/1991 | Kuwana et al. | 73/61.10 R |
| 5,196,340 | 3/1993 | Miyamoto | 435/288 |

OTHER PUBLICATIONS

"Mercury (II) and Silver (I) Ion-Selective . . . ", Lai et al., *The Analyst* vol. 111, No. 8 Aug. 86, pp. 891–894.
"Preconcentration and Determination of Lead (II) at . . . " Prabhu et al., *Electroanalysis* (N.Y.), 1(1) 13–21.
"Polarographic study of the interaction between . . . " Paraham et al., J. Electroanal. Chem. 314 (1991) 71–80.

*Primary Examiner*—James C. Housel
*Assistant Examiner*—Rachel Freed
*Attorney, Agent, or Firm*—Hana Dolezalova

[57] ABSTRACT

A highly specific and sensitive electrode for the determination of ultra-low levels of mercury and an analytical system based on such electrode. The electrode is a glassy carbon electrode spin-coated with a monolayer of a highly sensitive reagent for the detection of mercury. The analytical method based on the use of this type of electrode is a voltammetric method. Concentrations of the order of as low as about $2.10^{-12}$ Moles mercury can be detected and measured. The reagent is 4,7,13,16,21,24-hexaoxa-1,10-diazabicyclo-[8.8.8]hexacosane.

4 Claims, 1 Drawing Sheet

DETERMINATION OF ULTRA LOW LEVELS OF MERCURY

FIELD OF THE INVENTION

There is provided a highly specific electrode for the determination of ultra-low levels of mercury. There is further provided a system for the determination of ultra-low levels of mercury in a variety of media.

BACKGROUND OF THE INVENTION

Current environmental concern from the danger of mercury pollution, has drawn remarkable efforts toward developing analytical methods for this metal. To determine the levels of mercury in our environment, very sensitive, as well as selective methods, must be employed. For example, the concentration of mercury in sea water can be as low as $2 \times 10^{-12}$M. As a result, most known methods require a preconcentration step. On the other hand, some samples need a pretreatment step to separate mercury from other interferences due to low selectivity of the applied method. These requirements substantially increase the time of analysis. In addition, and as a consequence of these low levels, the analyst encounters problems that influence the reliability of the results, such as sample preservation and contamination from reagents.

Mercury is one of the elements which has been concentrated and determined electrochemically on modified electrodes. One of the most sensitive electroanalytical techniques. i.e. anodic stripping voltammetry (a.s.v.) has been successfully applied to determine $10^{-9}$M [Gao, Z., Li, P., Zhao, Z. Microchem. J. 43, 121–132 (1991)] and $5-10^{-11}$M [Liu, K., Wu, Q., Liu., H. Analyst 115, 835-837 (1990)] of mercury using modified electrodes. Nevertheless, laborious preparation and conditioning of electrodes, synthesis of organic reagents and insufficiently high selectivity have discouraged the wide application of a.s.v. for the routine determination of mercury.

SUMMARY OF THE INVENTION

There are provided means for the determination of ultra-low level concentrations of mercury in various media. There is further provided a highly specific ultra-sensitive electrode for such determinations. The term "ultra-low level" used in this context means concentrations of the order of about $2 \times 10^{-12}$M mercury in an aqueous medium, such as sea water. The novel electrodes and determination system are not disturbed by the presence of certain metal ions, even at much higher levels than the level of the mercury.

According to a preferred embodiment of the invention there is provided a glassy-carbon electrode (GCE) coated with 4, 7,13,16,21,24-hexaoxa-1,10-diazabicyclo[8.8.8]hexacosane, known as KRYPTOFIX-22 ™ Gill, G. A., Fitzgerald, W. F. Global Blochem, Cycles 1. 199-212 (1987). Such electrodes are prepared by spin coating of previously polished glassy carbon electrodes. The coating can be effected by applying a few drops of a $5 \times 10^{-3}$M solution of KRYPTOFIX-222 in methanol to an area of about 0.07 cm² of such electrode while this is rotated at about 3000 RPM. This mode of application is highly reproducible. Other solvents of KRYPTOFIX-222 can also be used.

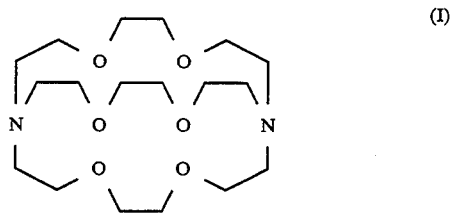

(I)

FIG. 1 shows the anodic stripping Osteryoung square wave voltammograms (OSWV) of sea water (Mediterranean; Israel) recorded with a KRYPTOFIX-222 modified GCE. A clear anodic peak associated with the oxidation of predeposited mercury is observed at 0.1 V versus Ag/AgCl. The concentration of mercury in sea water was estimated $(1.01 \pm 0.03) \times 10^{-11}$M using standard addition method. Control experiments confirmed that the modification of the electrode was essential for detecting these trace amounts of mercury. KRYPTOFIX-222 exhibits a fairly high affinity toward Hg(II). Electrodes have been modified by spin-coating them with a methanolic solution of KRYPTOFIX-222.

To confirm the results, as well as to verify the application of the novel method to the analysis of natural waters, simultaneous analyses have been accomplished by this method and by cold vapor flameless atomic absorption. Excellent agreement between the results obtained by both methods have been found. For example, the concentration of mercury in two samples was $0.75 \pm 0.06$ and $82.2 \pm 0.1$ ppb respectively as compared with 0.90 and 89.5 ppb, respectively, obtained by cold vapor atomic absorption.

These samples had to be diluted 450 and 45000 times, respectively, before the voltammetric analysis could be carried out.

The novel electrodes exhibit remarkable stability and, as a result can be applied for numerous determinations. The modified surface was electrochemically regenerated by soaking the electrode after each experiment in a mercury free solution for 1 min at 0.3 V or by cycling them between $\pm 0.3$ V. The relatively fast depletion of Hg(II) from the electrode upon its continuous electrocycling can be explained by the facile transport of mercury ions to the KRYPTOFIX-222. This is also supported by the fact that the same kinetics of Hg(II) reduction is observed when a bare or a modified electrode is employed. The excess of surface coverage, $\theta$, which was determined electrochemically ($\theta = 3.6 \times 10^{-10}$ mol, cm$^{-2}$) reveals that a monolayer rather than a film is formed.

The various parameters that govern the sensitivity of the method, such as the time and potential of deposition and the nature of the electrolyte, were investigated. Optimum conditions have been obtained by applying $-0.5$ V for 5 min. in 0.01M acetate buffer consisting of 0.1M NaCl.

Under the above-selected conditions, a good linear dependence was obtained between the stripping peak current and the concentration of mercury (II) ions in the concentration range of $1.5 \times 10^{-12} - 1.2 \times 10^{-11}$M with a detection limit of less than $10^{-12}$M (5 min. preconcentration time). The relative standard deviation was 3.3%. It should be pointed out, that the method exhibited similar sensitivity toward Hg(I) and Hg(II) and therefore yields the total levels of mercury in the analyte. To the best of our knowledge, the novel method represents the lowest detection limit ever reported for mercury (II) using an electrochemical technique. The detection limit of less than $10^{-12}M$ for mercury, can be compared only with the detection limit of expensive and relatively complicated methods, such as inductively coupled plasma/mass spectrometry.

Although high sensitivity is the dominant requirement from any analytical method, it must be accompanied also by high selectivity. The possible interferences from common metal ions and anions capable of complexing with KRYPTOFIX-222 or mercury (II) were examined. The determination of $10^{-11}M$ of mercury (II) ions was not affected by the addition of $10^{-5}M$ $ZN^{2+}$, $Cu^{2+}$, $Pb^{2+}$, $Cd^{2+}$, $Mn^{2+}$ and $10^{-7}M$ $Ag+$. The stripping peak current was slightly decreased upon the addition of more than $10^{-6}M$ $Cr^{3+}$. Anions, such as acetate, chloride and thiocyanate did not interfere with the electrochemical response of the modified electrode.

The modified electrodes offer a simple, fast and reliable means for monitoring mercury in our environment.

Figure 1:
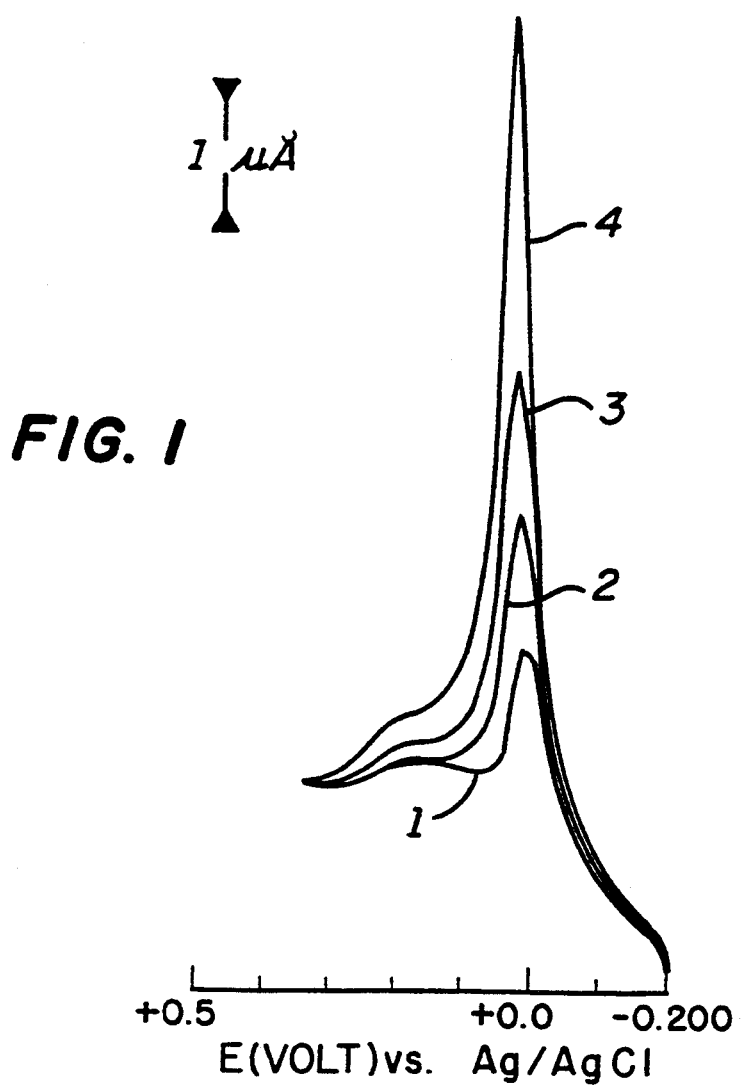
FIG. 1: Anodic O-square wave stripping voltammongrams of a GCE coated with Kryptofix-222 in a solution of 0.01M acetate buffer (pH4.0): (1)—sea water; upon addition of (2)—$7.7 \times 10^{-12}M$ Hg (II); (3)—$1.5 \times 10^{-11}M$ Hg (II); (4)- $2.9 \times 10^{-11}M$ Hg (II).
Figure 2:
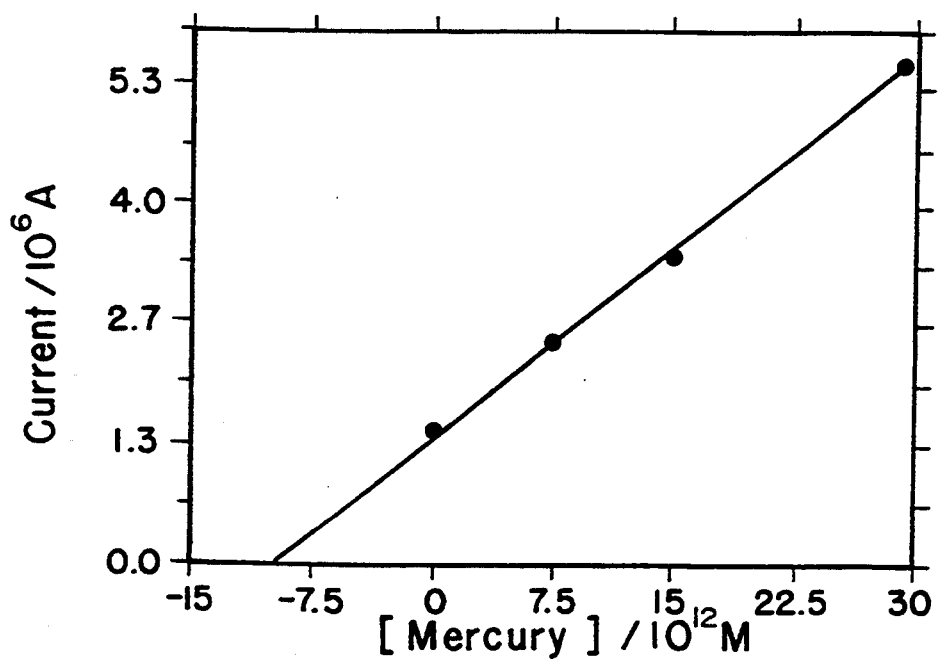
FIG. 2: Anodic peak currents of mercury as a function of mercury concentration in sea water before and after standard addition. Potential and time of deposition equal $-0.5$ V and 300 s respectively, a.c. amplitude 50 mV, frequency 15 Hz and potential step 6 mV.

We claim:

1. A highly specific and sensitive electrode for a quantitative determination of ultra-low concentration levels of about $2 \times 10^{-12}M$ of mercury in aqueous media, consisting of a glassy-carbon electrode spin-coated with a monolayer of 4,7,13,16,21,24-hexaoxa-1,10-diazabicyclo-[8.8.8]hexacosane reagent.

2. An electrode according to claim 1, spin-coated with the layer of the reagent from a solution of the reagent in an organic volatile solvent.

3. The electrode according to claim 2 having a specificity for detection of ultra-low levels of about $2 \times 10^{-12}M$ of mercury in the presence of zinc, copper, lead, cadmium, manganese or silver ions in concentration up to $10^{-5}M$.

4. The electrode of claim 2, spin-coated with a methanolic solution of the reagent.

* * * * *